United States Patent [19]

Johnson et al.

[11] Patent Number: 5,429,627
[45] Date of Patent: Jul. 4, 1995

[54] REUSABLE FEMININE HYGIENE SYSTEM

[75] Inventors: Stacey A. Johnson; Kirk A. Johnson, both of Brier, Wash.

[73] Assignee: Lotus Trading Company, Seattle, Wash.

[21] Appl. No.: 57,533

[22] Filed: May 4, 1993

[51] Int. Cl.⁶ .................. A61F 13/15; A61F 13/20
[52] U.S. Cl. .................. 604/358; 604/378; 604/385.1; 604/391; 604/393; 604/397; 604/402; 270/41
[58] Field of Search .............. 604/358, 378, 381–382, 604/385.1, 391, 393, 397, 398, 399, 402; 270/32, 37, 40, 41

[56] References Cited

U.S. PATENT DOCUMENTS

| | | | |
|---|---|---|---|
| 3,719,189 | 3/1973 | Sherman | 604/381 |
| 4,678,465 | 7/1987 | Avejic | 604/397 |
| 5,019,068 | 5/1991 | Perez et al. | 604/393 |
| 5,106,382 | 4/1992 | Henry | 604/391 |
| 5,181,915 | 1/1993 | Smith | 604/385.1 |
| 5,261,900 | 11/1993 | Houle et al. | 604/385.1 |

OTHER PUBLICATIONS

New Cycle—Menstral Wealth Catalogue, Spring 1992 by Tamara Slayton.

*Primary Examiner*—Randall L. Green
*Assistant Examiner*—P. Zuttarelli
*Attorney, Agent, or Firm*—Michael J. Folise

[57] ABSTRACT

Reusable, washable feminine napkins and panty liners have multiple absorbent layers encasing a fluid imperiable layer. The napkin has a side opening pocket for an extra absorbent filler pad. Both the napkin and the panty liner employ a centrally located mounting device which is not connected to the fluid imperiable layer.

17 Claims, 2 Drawing Sheets

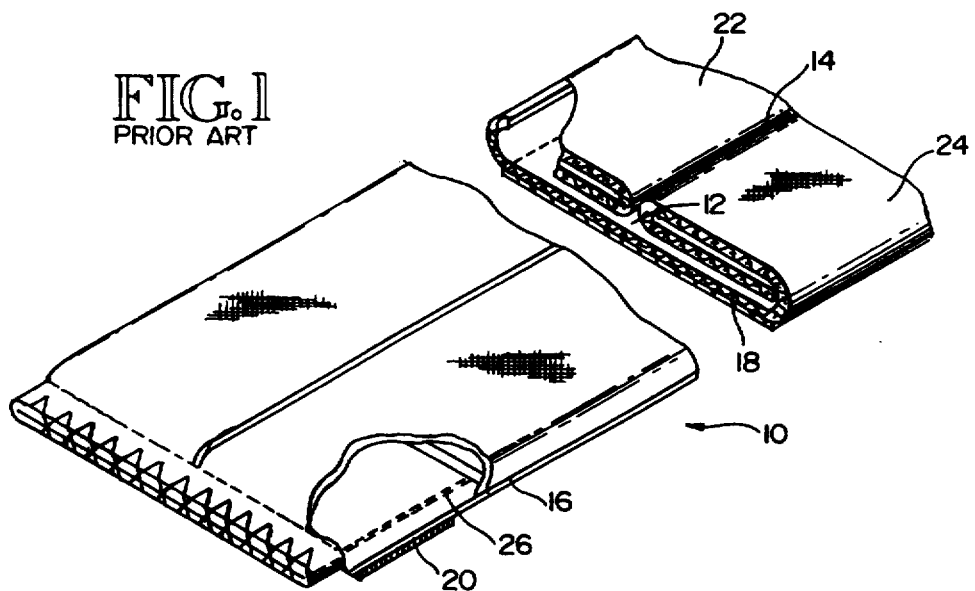
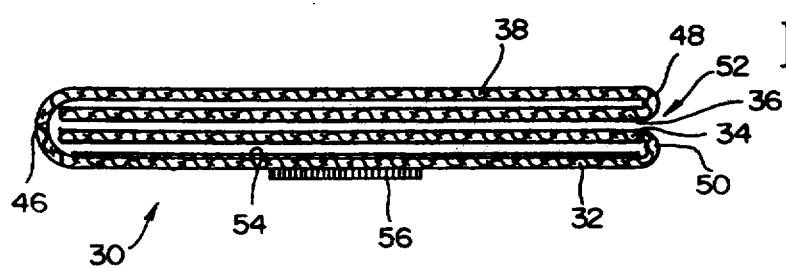
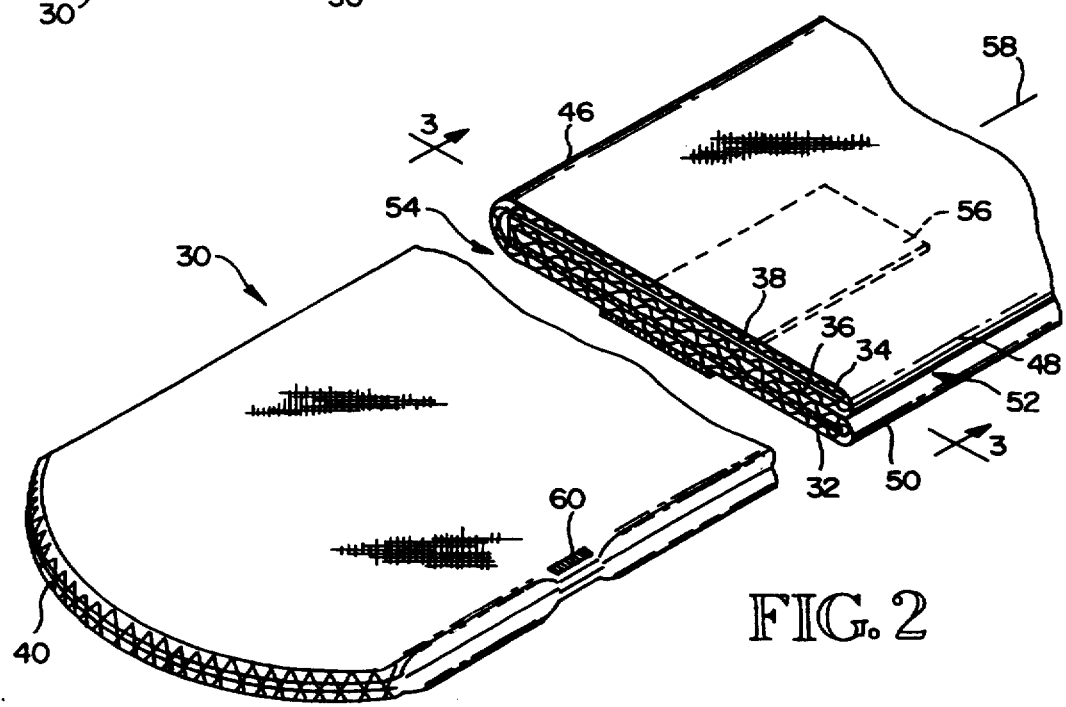

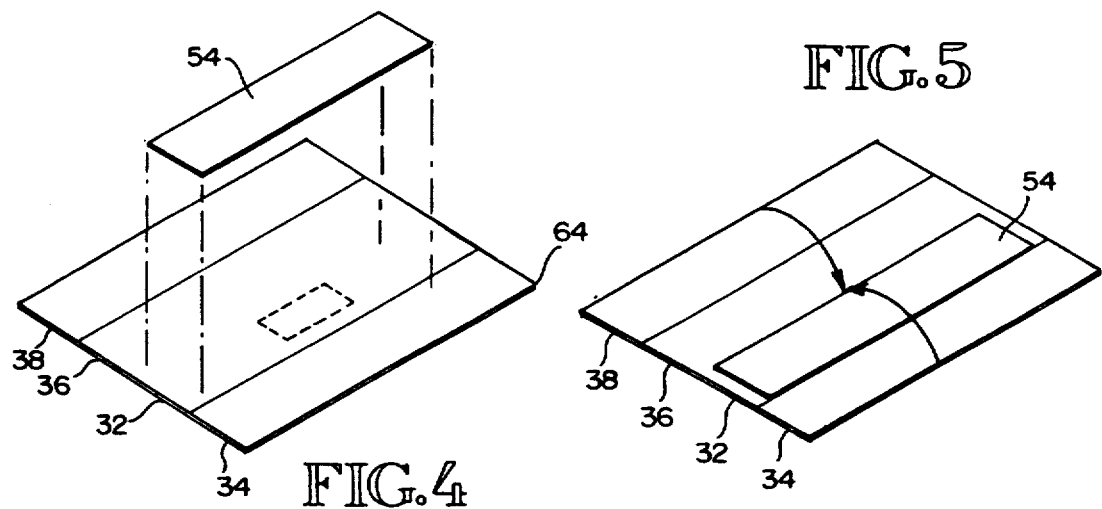
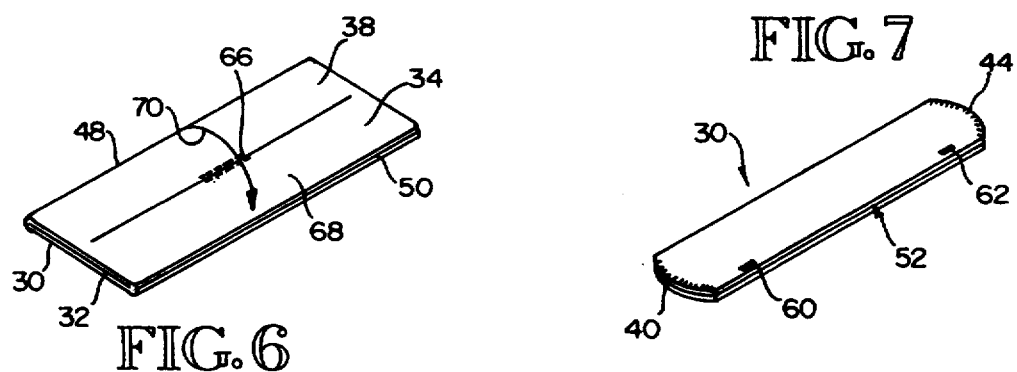
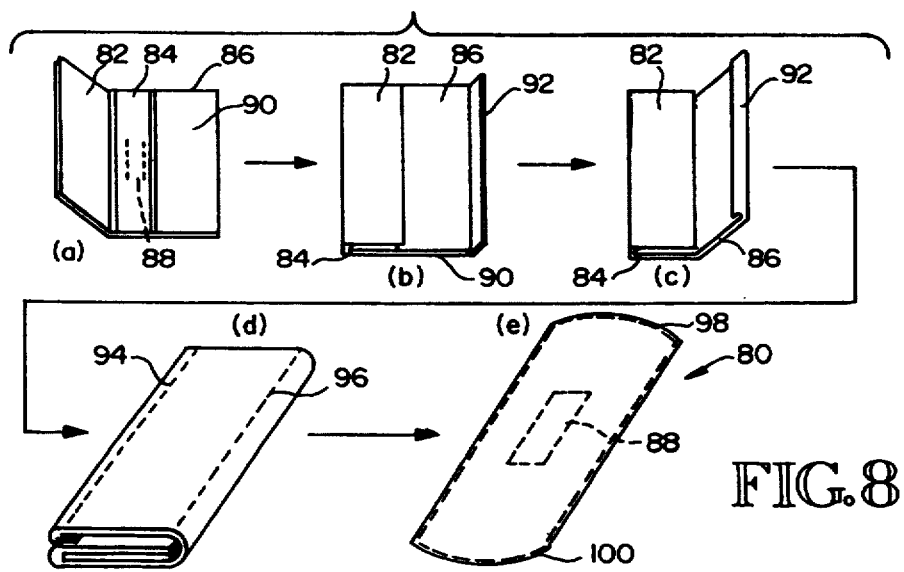

5,429,627

REUSABLE FEMININE HYGIENE SYSTEM

TECHNICAL FIELD

The invention relates to reusable sanitary napkins and undergarment shields. More specifically, the invention relates to multi-layer sanitary napkins and undergarment shields.

BACKGROUND OF INVENTION

For over thirty years American women have favored disposable sanitary napkins which are worn outside of the body, and even more so lately, disposable tampons, which are worn inside the vaginal canal to absorb the flow of fluids during menstruation. Recently, due to a combination of environmental and health concerns, a growing minority of women have shown a preference for reusable, washable sanitary napkins.

The health problems associated with the use of disposable tampons in particular has ironically grown with the increasing technical effectiveness and absorbency of the latest products. Modern, super absorbent, disposable tampons are so absorbent and leak proof that users are often unaware that their tampon has become saturated and is ready for removal. As a result, some users do not replace these tampons frequently enough to avoid the explosive bacterial growth which is possible in the anaerobic environment within the vaginal canal. Toxins released by these bacteria can result in a shock syndrome in a small minority of women, leading to severe illness.

As a result of the above described health problem, and for those women who are at risk, the option of externally worn, disposable sanitary napkins has been revisited. Although these products have been available for sometime and have performed their functions adequately, environmental concerns regarding disposable products now occupy a higher level of public concern. Solid waste landfills in some metropolitan areas are filled to capacity and cannot accommodate the high volume of biologically contaminated waste products, such as, disposable diapers, sanitary napkins and tampons, generated by a modern metropolitan area.

Various businesses have developed washable, reusable, feminine hygiene products which avoid the environmental and health related problems discussed above. New Cycle Products, Sebastopol, Calif. manufactures a line of flannel and terry cloth pads which may be worn in the crotch area of women's undergarments. Some of these products are elongated, elliptical pads while others are square cotton pads having extra material in the center sections thereof. The square pads may be folded to increase the thickness and enhance absorbency for the pads when required. Unfortunately, these products suffer from many of inconveniences which caused women to adopt disposable products over non disposable napkins during the past 30 years. These problems are principally: a tendency for the pads to shift while being worn resulting in a loss of protection; external belts or other uncomfortable devices required to secure the washable pads in place; and, a high probability that during a heavy flow, the reusable pads will become saturated before they can be changed resulting in soiling of the undergarment.

One manufacturer, Modern Woman's Choice, Vancouver, Canada has addressed these problems with a design shown in FIG. 1. Modern Woman's Choice reusable, washable sanitary napkin is generally indicated at reference numeral 10 in FIG. 1. The napkin is manufactured from a single sheet of cotton fleece material which is folded in on itself, so as to form a pocket 12 accessible by way of longitudinal slot 14 for insertion of an extra liner pad (not shown) for heavy flow days. The entire napkin 10 is generally rectangular in shape having a length of approximately seven inches and a width of approximately three inches.

To prevent flow-through of fluid if the napkin becomes saturated, even with a filler pad in the pocket 12, a layer of fluid impervious cloth 16 is sewn to the lower most (outer most, when worn) layer 18. To secure the napkin 10 to a women's undergarments, a hook portion 20 of a hook and loop type closure system is sewn to the distal ends of the napkin to both the fluid impervious cloth 16 and the outer most flannel layer 18. The corresponding loop portions of the closure device are sewn to appropriate locations on the undergarment for proper positioning of the napkin.

The Modern Women's Choice sanitary napkin 10 described above suffers from three principle limitations. The first limitation results from the mechanical structure of the napkin which bifurcates the same by longitudinal slot 14, so as to create the pocket 12. It has been found that after repeated washings, the napkin 10 and hence the pocket begin to lose their shape making insertion of the filler pad (not shown) into the pocket 12 difficult and causing left and right flap portions 22, 24 to separate thereby creating a gap exactly in the area where the heaviest menstrual flow is expected. By sewing through the fluid impervious cloth at longitudional and lateral sews line 26 to secure the hook portion 20 to the napkin 10, the fluid impervious nature of the cloth 16 is seriously compromised allowing fluids to leak through. Finally, the cloth 16 is generally a coated nylon cloth having relatively sharp edges. The lateral edges are completely exposed to the inner thigh and groin area. Skin in this area is highly sensitive and after wearing the napkin 10 for a long period, chaffing can become a serious discomfort.

Therefore, a need exists for a reusable feminine hygiene system, which is absorbent, fluid impervious and comfortable to wear.

SUMMARY OF INVENTION

It is therefore an object of the present invention to provide a reusable, washable feminine hygiene system which retains its shape after repeated washings.

It is another object of the present invention to achieve the above object in a structure which is comfortable to wear and does not have any sharp or rough edges exposed.

It is yet another object of the present invention to achieve the above objects in a structure which is impervious to the passage of fluids therethrough.

It is yet a further object of the invention to achieve the above objects in a design which is aesthetically pleasing and feminine in character.

The invention achieves these objects and other objects and advantages which will become apparent from the description which follows by providing a construction method which results in a reusable, washable, feminine hygiene napkin or panty liner, having a multi-layer construction. An attachment device is provided which is connected only to the outer most layer (as worn) so that a fluid impermeable layer contained within the multiple absorbent layers is not compromised. The construction method employed results in a feminine hygiene napkin or panty liner having curved, rolled, peripheral edges which are comfortable against the skin of a woman.

In a preferred embodiment of the invention, three of the four peripheral edges are closed while the fourth peripheral edge is provided with an opening for insertion of an absorbent, optional filler pad for placement into an interior pocket. The structural integrity of the napkin is maintained by providing this opening on the side.

In alternate embodiments, a panty liner without the interior pocket is disclosed.

BRIEF DESCRIPTION OF THE DRAWINGS

FIG. 1 is a partial, isometric view of a prior art reusable feminine napkin with portions cut away.

FIG. 2 is an isometric view of a reusable, washable, feminine hygiene napkin employing the concepts of the present invention with portions cut away.

FIG. 3 is a side elevational view of the feminine hygiene napkin shown in FIG. 2 and taken along line 3—3.

FIGS. 4 through 7 are schematic, isometric assembly diagrams of the reusable, washable, feminine hygiene napkins shown in the FIGS. 2 and 3.

FIG. 8 is a schematic, isometric assembly diagram of a panty liner employing the concepts of the present invention.

DETAILED DESCRIPTION OF THE PREFERRED EMBODIMENTS

A reusable, washable, feminine hygiene napkin employing the principles of the present invention is generally indicated at reference numeral 30 in FIGS. 2 and 3. The napkin has a first, outermost (as worn) layer 32, second and third intermediate absorbent layers 34 and 36, respectively; and uppermost (or top) absorbent layer 38. The layers are preferably manufactured from a single sheet of flannel or other absorbent, organic textile material having the softest side facing outwardly.

As best seen in FIGS. 2, 3 and 7, the napkin 30 has peripheral ends 40, 44 which are closed by a surge stitching technique to be described in further detail below. A left lateral edge 46 presents a smooth curved surface to the user. A right peripheral edge is formed by upper and lower peripheral edges 48, 50 respectively, which define a pocket, generally indicated at reference numeral 52. The pocket 52 is adapted for receipt of an optional, absorbent filler pad (not shown) for extra absorbency.

To prevent flow-through of menstrual fluids even if the napkin 30 becomes saturated, a fluid impervious layer 54 is totally enclosed between the first and second layers 32, 34 peripheral edges 46 and 50, and surge stitched ends 40 and 44 of the napkin. This layer preferably consists of a sheet of poly-vinyl chloride coated nylon sheeting, or alternatively a coating applied directly to the underside of layer 34 (i.e. outwardly directed side as worn) or the top of layer 32 (the inwardly directed side as worn) in the orientation shown in FIG. 3. As should now be apparent, the first layer 32 need not be absorbent because the fluid impervious layer 54 substantially prevents saturation of the first layer, although softness and absorbency of the first layer is preferred.

To prevent perforation of the fluid impervious layer 54 the hook portion of a hook and loop closure element 56 is sewn only to the first layer 32 so that the fluid impervious nature of the layer 54 is not compromised.

In addition, the closure element 56 is aligned along the major axis, represented by line 58 intermediate the ends 40, 44 so as to be displaced from the lateral edges and ends of the napkin where they are unlikely to chaff a women's thighs. The mating loop portion (not shown) is sewn into the crotch area of the woman's undergarment also in a longitudinal manner to permit significant longitudinal adjustment of the napkin 10 with respect to the user's undergarment. Bar tacks 60 and 62 shown in FIGS. 2 and 7 are positioned approximately one inch inwardly from the ends 40, 44 along the length of the pocket opening 52 so that the optional, absorbent filler pad (not shown) is reasonably secure within the pocket when in use.

The structure described above possesses three distinct advantages over prior art designs. The side opening pocket 52 for accepting the filler pad has been found to withstand repetitive washings while still maintaining the general shape of the napkin 10 as shown in the drawings. The pocket is not prone to open up as the napkin 30 is bent out of the plane of the paper shown in FIG. 2 when the napkin is actually in use. Thus, all of the absorbent layers remain in place to absorb menstrual flow. The second advantage relates to the total encapsulation of the fluid impervious layer 54 between the first and second layers 32, 34. There are no rough or sharp edges to chaff against the thighs. Finally, as will be described in further detail below, the hook closure device 56 is sewn only to the outermost absorbent layer 32, and not to the inner fluid impervious layer 54 so as not to compromise the effectiveness of the fluid impervious layer.

The construction technique employed to produce the products shown in FIGS. 2 and 3 is shown sequentially in FIGS. 4 through 7. In a first series of steps shown in FIG. 4, a single sheet 64 of 8.5 ounce cotton fleece material cut to the appropriate dimensions is placed on a surface. The sheet is divided into four substantially equal panels which will form the first through fourth absorbent layers 32, 34, 36, 38 and are numbered accordingly. The hook portion 56 of the hook and loop closure is sewn into the middle on the underside (fuzzy side) of the first panel 32. The fluid impervious panel 54 is then placed on top of the first panel on the non-fuzzy side of the sheet 64.

As shown in FIG. 5, the outermost panels 34, 38 are folded inwardly over the inner most panels 32, 36 to assume the configuration shogun in FIG. 6. Note that the lateral edges of this intermediate construction stage (FIG. 6) will eventually form the upper and lower edges 48 and 50 shown in FIG. 2 and that these edges are now rounded with the fuzzy side of cotton fleece facing outwardly. As best seen in FIG. 6, the panels are lightly tacked at stitches 66, 68 which will hold the construction together at this intermediate stage and to maintain the shape of the pad during washing. Next, panels 36 and 38 are folded over panels 32 and 34 as shown by arrow 70 to assume the configuration shown in FIG. 7. The ends 40 and 44 are then sewn with a "surge stitching" machine which places a lock stitch on the edges while curving and trimming the edges at the same time. It is these surge stitches on the peripheral ends 40, 44 which hold the fluid impervious layer 54 in place. Thus, the central area of the fluid impervious layer has not been perforated or compromised by any stitching whatsoever and will remain fluid impervious throughout the lifetime of the napkin.

Finally, the bar tacks 60 and 62 are placed approximately one inch in from the peripheral ends 40, 44 to partially close the pocket opening 52 so as to adequately retain the optional, absorbent filler pad (not shown) in place when necessary.

The construction technique described above for the washable feminine hygiene napkin 30 can also be employed to produce a panty liner generally indicated at reference numeral 80, in FIG. 8 for use on days when menstrual flow is de minimus.

In a first step (a), a single sheet of cotton fleece material 82 is divided into first, second and third panels, 82, 84 and 86 respectively of essentially equal dimensions. The third panel 86 is slightly wider (approximately one quarter inch) than the first and second panels. A hook closure device 88 is sewn onto the reverse side of the second panel 84 (fuzzy side). The entire structure is then turned over as shown in the first step (a) and a fluid impervious sheet 90 is positioned on the second panel 84.

As shown in step (b) the first panel is folded on top of the second panel 84 and the fluid impervious sheet 90. A one quarter inch lip portion 92 of the third panel 86 is then folded inwardly as more fully shown in step (c). The third panel 86 is folded over at lip portion 92 and then folded on top of the first and second panels as shown in step (d). Single stitches 94 and 96 are then run longitudinally along the lateral edges of the structure as shown in step (d) to consolidate and stabilize the structure. Finally, as shown in step (e) the peripheral ends 98, 100 are surge stitched to provide the desired curved shape and closed ends.

The resulting panty liner 80 manufactured by this technique enjoys advantages similar to the those enjoyed by the napkin design 30. Specifically, the fluid impervious layer 84 is totally enclosed within the panty liner 80 thus avoiding rough edges against the skin and chaffing. The hook closure device 88 is laterally and longitudinally placed in the center of the liner and thus avoids touching the legs or the groin area. Finally, the lateral edges of the liner are rounded and smooth as shown in FIG. 8, step (d) thus providing the user with maximum comfort.

Those with ordinary skill in the art will appreciate that other embodiments and variations of the invention are possible which employ the same inventive concepts described above. Therefore, the invention is not to be limited by the above disclosure but is to be determined in scope by the claims which follow.

I claim:

1. A reusable, washable feminine hygiene napkin, comprising:
    first lowermost, second and third intermediate and fourth uppermost relatively soft, absorbent layers positioned in registration with one another and interconnected so as to define an elongated pad having three closed peripheral edges and wherein the fourth uppermost layer is laterally coextensive with the first layer so as to form a fourth, elongated peripheral edge having an opening defining a side accessible pocket between the second and third layers for introduction of an optional absorbent filler pad therein;
    an interior, fluid impermeable layer positioned between the first and second layers; and,
    an undergarment attachment device connected only to the first lowermost layer so that the fluid impermeable layer is not compromised and for securing the napkin to a women's undergarment.

2. The feminine hygiene napkin of claim 1, wherein the first through fourth layers are formed by a single continuous sheet of textile material and wherein the second and third intermediate layers are coextensive with the first and second layers and are folded over potions of the lowermost first and uppermost fourth layers so that the resultant two elongated lateral edges of the pad have comfortable, curved exposed edges.

3. The feminine hygiene napkin of claim 2, wherein the fluid impermeable layer is a sheet of fluid impermeable material which is totally encapsulated by the folded over portion of the first lowermost and the second intermediate layer to isolate the sheet of fluid impermeable material from direct contact with a women's inner thighs.

4. The feminine hygiene napkin of claim 2, wherein the fluid impermeable layer is a plastic material adhered to an outwardly directed side of the second layer and wherein the impermeable layer is totally encapsulated by the folded over portion of the first lowermost and the second intermediate layer to isolate the substantially fluid impermeable layer from direct contact with a women's inner thighs.

5. The feminine hygiene napkin of claim 2, wherein the fluid impermeable layer is a plastic material adhered to an inwardly directed side of the first layer and wherein the impermeable layer is totally encapsulated by the folded over portion of the first lowermost and the second intermediate layer to isolate the substantially fluid impermeable layer from direct contact with a women's inner thighs.

6. The feminine hygiene napkin of claim 1, wherein the attachment device is elongated, is connected only to the first lowermost layer and is substantially laterally aligned with a longitudinal axis of the pad and is located away from the peripheral edges of the pad so that the attachment device is not likely to contact a women's inner thighs when the pad is in use.

7. The feminine hygiene napkin of claim 1, wherein the attachment device is a hook and loop closure element connected to a central, exposed area of the first textile layer and wherein the closure element is not directly connected to the fluid impermeable layer.

8. A reusable, washable panty liner, comprising:
    first lowermost, second intermediate and third uppermost substantially equidimensional layers folded from a single sheet of relatively soft, absorbent material, the panty liner defining two longitudinal edges after folding and having a lip folded over from the third outermost layer so as to be adjacent to the second intermediate layer at one of the longitudinal edges where all four edges of the liner are sewn closed after folding to define an elongated panty liner pad having four sewn closed peripheral, rounded edges, the two longitudinal edges being sewn inwardly from the longitudinal edges;
    an interior, fluid impermeable layer positioned between the first and second layers; and,
    an undergarment attachment device connected only to the first lowermost layer so that the fluid impermeable layer is not compromised and for securing the napkin to a woman's undergarment.

9. The reusable parity liner of claim 8, wherein the fluid impermeable layer is a sheet of substantially fluid impermeable material which is totally encapsulated by the folded over portion of the first lowermost and the second intermediate layer to isolate the sheet of substantially fluid impermeable material from direct contact with a woman's inner thighs.

10. The reusable panty liner of claim 8, wherein the fluid impermeable layer is a plastic material adhered to an outwardly directed side of the second textile layer and wherein the impermeable layer is totally encapsulated by the folded over portion of the first lowermost and the second intermediate layer to isolate the substantially fluid impermeable layer from direct contact with a woman's inner thighs.

11. The reusable panty liner of claim 8, wherein the fluid impereable layer is a plastic material adhered to an inwardly directed side of the first layer and wherein the impereable layer is totally encapsulated by the folded over portion of the first lowermost and the second intermediate layer to isolate the substantially fluid impermeable layer from direct contact with a woman's inner thighs.

12. A reusable, washable feminine hygiene product made by a process comprising the following steps:
    dividing a continuous sheet of relatively flat, soft, absorbent material into at least three equidimensional panels;
    connecting an attachment device to a central portion of an inner one of the at least three panels;
    turning the sheet over;
    positioning a substantially fluid impermeable layer on the inner one of the at least three panels opposite the attachment device;
    folding an adjacent outermost panel over the inner panel having the fluid impermeable layer;
    folding any remaining panels over the already folded panels; and
    securing the panels together.

13. The feminine hygiene product made by the process of claim 12, wherein the sheet is divided into four equidimensional panels, and outermost panels are folded in on the innermost panels and remaining doubled over halves are folded together and bar tacked to form an elongated pad having three closed peripheral edges and a forth, elongated substantially open peripheral edge defining a side accessible pocket for introduction of an optional absorbent filler pad therein.

14. The feminine hygiene product made by the process of claim 12, wherein the sheet is divided into four panels, three being equidimensional and the fourth being a substantially narrower panel, two of the panels being outermost and two of the panels being innermost including the steps of folding outermost panels in on innermost panels and folding remaining doubled over portions together so as to form three open edges and closing the three open edges to form an elongated panty liner pad having four closed peripheral edges.

15. A method for making a reusable, washable feminine hygiene product made by a process comprising the following steps:
    dividing a continuous sheet of relatively soft, absorbent material into at least three substantially equidimensional panels;
    connecting an attachment device to a central portion of an inner one of the at least three panels;
    turning the sheet over;
    positioning a substantially fluid impermeable layer on the inner one of the at least three panels opposite the attachment device;
    folding an adjacent outermost panel over the inner panel having the fluid impermeable layer;
    folding any remaining panels over the already folded panels; and,
    securing the panels together.

16. The method of claim 15, wherein the sheet is divided into four equidimensional panels, the outermost panels are folded in on the innermost panels and the remaining doubled over halves folded together and bar tacked to form an elongated pad having three substantially closed peripheral edges and a fourth, elongated substantially open peripheral edge defining a side accessible pocket for introduction of an optional absorbent filler pad therein.

17. The method of claim 15, wherein the sheet is divided into four panels, three being substantially equidimensional and the fourth being substantially narrower panel including the steps of folding the outermost panels in on the innermost panels and folding the remaining doubled over portions together so as to form three open edges and closing the three open edges to form an elongated panty liner pad having four substantially closed peripheral edges.

* * * * *